United States Patent
Campbell et al.

(10) Patent No.: US 7,475,989 B2
(45) Date of Patent: Jan. 13, 2009

(54) SHACK-HARTMANN BASED INTEGRATED AUTOREFRACTION AND WAVEFRONT MEASUREMENTS OF THE EYE

(75) Inventors: Charles C. Campbell, Berkeley, CA (US); Seema Somani, Milpitas, CA (US)

(73) Assignee: AMO Manufacturing USA, LLC, Santa Clara, CA (US)

(*) Notice: Subject to any disclaimer, the term of this patent is extended or adjusted under 35 U.S.C. 154(b) by 197 days.

(21) Appl. No.: 11/376,725

(22) Filed: Mar. 14, 2006

(65) Prior Publication Data

US 2007/0216867 A1 Sep. 20, 2007

(51) Int. Cl.
*A61B 3/00* (2006.01)

(52) U.S. Cl. .................. 351/246; 351/205; 351/209; 351/210

(58) Field of Classification Search ............... 351/205, 351/209, 212, 216, 217, 246, 247
See application file for complete search history.

(56) References Cited

U.S. PATENT DOCUMENTS

| | | | |
|---|---|---|---|
| 6,050,687 A | 4/2000 | Bille et al. | |
| 6,070,981 A | 6/2000 | Mihashi et al. | |
| 6,554,429 B1 | 4/2003 | Campin et al. | |
| 6,572,230 B2 * | 6/2003 | Levine | 351/221 |
| 6,598,974 B2 | 7/2003 | Jones et al. | |
| 6,609,794 B2 * | 8/2003 | Levine | 351/221 |
| 6,709,108 B2 | 3/2004 | Levine et al. | |
| 6,715,877 B2 | 4/2004 | Molebny | |
| 6,924,792 B1 | 8/2005 | Jessop | |
| 2001/0016695 A1 | 8/2001 | Mihashi et al. | |
| 2003/0007127 A1 * | 1/2003 | Levine | 351/212 |
| 2005/0099599 A1 | 5/2005 | Mihashi et al. | |
| 2005/0248849 A1 * | 11/2005 | Urey et al. | 359/619 |
| 2005/0275946 A1 * | 12/2005 | Choo et al. | 359/619 |
| 2005/0285835 A1 | 12/2005 | Jessop | |
| 2006/0106426 A1 | 5/2006 | Campbell | |

* cited by examiner

*Primary Examiner*—Ricky L Mack
*Assistant Examiner*—James R Greece
(74) *Attorney, Agent, or Firm*—Townsend and Townsend and Crew LLP

(57) ABSTRACT

Devices, systems, and methods often by measuring characterize optical structures and systems, the standard refractive error and irregular aberrations. A retinal spot can propagate through optical tissues of an eye and can be directed to refractive correction optics for correcting standard refractive errors. The corrected image is then directed to wavefront analysis optics, which form a coarse pitch lenslet array pattern and a fine pitch lenslet array pattern. The coarse pitch pattern indicates the standard refractive error of the eye, and can be used to adjust the refractive correction optics. The fine pitch pattern is formed with the corrected retinal image, facilitating precise wavefront reconstruction, measurement of high order aberrations, and the like. The coarse pitch pattern and fine pitch pattern may be formed sequentially or simultaneously.

27 Claims, 7 Drawing Sheets

SHACK-HARTMANN BASED INTEGRATED AUTOREFRACTION AND WAVEFRONT MEASUREMENTS OF THE EYE

BACKGROUND OF THE INVENTION

The present invention is generally related to measurements of optical tissues. In exemplary embodiments, the invention provides devices, systems, and methods for measuring optical errors of eyes, particularly for determining higher order refractive aberrations of the optical tissues of the eyes and/or other optical structures.

Known laser eye surgery procedures generally employ an ultraviolet or infrared laser to remove a microscopic layer of stromal tissue from the cornea of the eye. The laser typically removes a selected shape of the corneal tissue, often to correct refractive errors of the eye. Ultraviolet laser ablation results in photodecomposition of the corneal tissue, but generally does not cause significant thermal damage to adjacent and underlying tissues of the eye. The irradiated molecules are broken into smaller volatile fragments photochemically, directly breaking the intermolecular bonds.

Laser ablation procedures can remove the targeted stroma of the cornea to change the cornea's contour for varying purposes, such as for correcting myopia, hyperopia, astigmatism, and the like. Control over the distribution of ablation energy across the cornea may be provided by a variety of systems and methods, including the use of ablatable masks, fixed and moveable apertures, controlled scanning systems, eye movement tracking mechanisms, and the like. In known systems, the laser beam often comprises a series of discrete pulses of laser light energy, with the total shape and amount of tissue removed being determined by the shape, size, location, and/or number of laser energy pulses impinging on the cornea. A variety of algorithms may be used to calculate the pattern of laser pulses used to reshape the cornea so as to correct a refractive error of the eye. Known systems also make use of a variety of forms of lasers and/or laser energy to effect the correction, including infrared lasers, ultraviolet lasers, femtosecond lasers, wavelength multiplied solid-state lasers, and the like. Alternative vision correction techniques make use of radial incisions in the cornea, intraocular lenses, removable corneal support structures, and the like.

Known corneal correction treatment methods have generally been successful in correcting standard vision errors, such as myopia, hyperopia, and astigmatism. However, as with all successes, still further improvements would be desirable. Toward that end, wavefront measurement systems are now available to measure the refractive characteristics of a particular patient's eye. By customizing an ablation pattern based on wavefront measurements and providing improved laser system calibration, it may be possible to correct minor refractive errors so as to reliably and repeatably provide visual accuities greater than 20/20.

Known wavefront measurement methods often involve a somewhat time-consuming process to perform high precision measurements of the total aberrations of a patient's eye. So as to provide high-precision measurements of the irregular or high-order aberrations of the eye, the standard or spherocylindrical error may be largely corrected within the wavefront system. Existing wavefront techniques generally seek to limit the sphero-cylindrical error of the measured wavefront to about a diopter or less by compensating for standard errors of the eye using refractive correction optics. When correcting the standard refractive error of the eye within a wavefront system, many systems search for the best focus of the wavefront array pattern spot images formed by the lenslet array of the wavefront sensor. Although such techniques can be quite effective, the delays in taking individual wavefront measurements can be inconvenient, and may limit the accuracy of the overall wavefront measurement, and hence the effectiveness of treatment prescriptions which are derived from those wavefront measurements.

In light of the above, it would be desirable to provide improved optical measurement devices, systems, and methods. It would be particularly beneficial if these improved techniques could build on the recent advances that have been made in wavefront measurement techniques, particularly if improvements in efficiency and/or accuracy of the measurements could be provided. Systems and methods which could avoid or obviate the need for time consuming iterative searches for the best focus of spot images within a lenslet array spot pattern would also be desirable, particularly if such advantages could be provided without the complexity or cost of a full auto-refractor integrated with the wavefront measurements optics, without having to resort to manual entry of standard optical corrections based on phoropter measurements, or the like.

BRIEF SUMMARY OF THE INVENTION

The present invention generally provides devices, systems, and methods for measuring and/or characterizing optical structures and systems. Exemplary embodiments provide systems and methods for measuring the standard refractive error and/or the irregular aberrations of an eye. A spot or other image formed on the retina propagates through the optical tissues of the eye and is directed to refractive correction optics, typically for correcting standard refractive errors such as myopia, hyperopia, and astigmatism. The corrected image is then directed to wavefront analysis optics, which often include both a coarse pitch lenslet array and a fine pitch lenslet array so as to form a coarse pitch array pattern and a fine pitch array pattern, respectively. The coarse pitch pattern generally indicates the standard refractive error of the eye, and can be used to adjust the refractive correction optics. The fine pitch pattern is formed using the corrected retinal image, facilitating precise wavefront reconstruction, measurement of high order aberrations, and the like. The coarse pitch pattern and fine pitch pattern may be formed sequentially or simultaneously, and the eye typically does not need to move between measurement of the standard refractive correction and a precision wavefront measurement. Advantageously, iterative searching and adjustments to the refractive correction optic so as to obtain the best focus within the fine pitch pattern spot images can optionally be avoided altogether, significantly increasing the speed and potentially the accuracy of an individual wavefront measurement. The complexity of a full auto-refractor integrated with the wavefront measurement optics, manual entry of standard refractive errors measured separately on the eye, and the like may be avoided.

In a first aspect, the invention provides a method for measurement of an eye. The eye has optical tissues with a spherocylindrical error and irregular aberration. The method comprises propagating a retinal image from the retina through the optical tissues. A first lenslet array pattern is generated from the image that is propagated through the tissues. The first pattern has a plurality, N, of retinal images. The spherocylindrical error of the eye is determined using the first pattern, and the retinal image is corrected per that sphero-cylindrical error. A second lenslet array pattern having a plurality, M, of retinal images is generated with the corrected retinal image. M is substantially greater than N. The irregular aberration of the eye is determined using the second pattern.

The first pattern is typically generated using a first lenslet array having a first pitch. The second pattern is often generated using a second lenslet array having a second pitch, with the first pitch being coarser than the second pitch. For example, the first pitch may be sufficiently coarser that M is at least twice N, M often being at least five times N. The retinal image may be directed from the tissues along one or more optical paths, with (for example) N lenses of the first array disposed within the optical path(s) of the retinal image, while M lenses of the second array are within the optical path(s) of the retinal image.

The retinal image typically propagates from the eye while the eye is at an eye measurement location. For example, an image may be formed on the retina using an infrared illumination source transmitting toward the eye location, with the retinal image typically comprising a small spot. This retinal image will generally propagate to the first lenslet array and to the second lenslet array without moving the eye from the eye measurement location. Advantageously, a wavefront of the eye can be measured without a search for a best focus spot for the various retinal images of the patterns. The retinal image may be sequentially directed to the first lenslet array and then to the second lenslet array, such as by reconfiguring at least one beam steering optic (for example, by moving a mirror or the like). A single image capture device may be used to sense both the first and second patterns by using a pair of moveable mirrors. In other embodiments, the first and second patterns may be generated simultaneous using first and second lenslet arrays, with the two patterns typically being sensed by two image capture devices.

The retinal image from the optical tissues may include a first portion of light which is directed to the first lenslet array and a second portion of light which is directed to the second lenslet array. The second portion of light (often associated with the finer pitch lenslet array) will generally be substantially greater than the first portion of light. For example, when there are at least four times as many images generated by the fine pitch lenslet array, the second portion of light directed toward that array may have at least four times the intensity of the first portion of light (associated with the coarse pitch array). More generally, each lenslet of the first array will often have a first area, and each lenslet of the second lenslet array will have a second area. The light from the optical tissues may be directed to a beam splitter, which directs the first portion of light to the first lenslet array and a second portion of light to the second lenslet array. A ratio of the intensity of the second portion of light to the first portion of light, as determined by the properties of the beam-splitter, should be at least as large as the ratio of the first area to the second area.

While the standard refractive errors in the retinal image may be corrected without searching for a best focus for the spots in the lenslet array patterns, the first lenslet array pattern may be used in a feedback loop to enhance sphero-cylindrical correction. For example, another first array pattern of retinal images may be generated from the corrected image, and a revised sphero-cylindrical error of the eye may be determined in response to the other first pattern. The revised sphero-cylindrical error of the retinal image may even be adjusted so that the first pattern is used in a sphero-cylindrical feedback correction loop. The standard refractive error may be used for generation of a refractive prescription of the eye, displayed to a system user, or the like. The determination of the sphero-cylindrical error of the eye from the first pattern may be performed in a variety of different ways, including by a simplified wavefront reconstruction using the limited number of image spot locations in the coarse pattern array, Zernike polynomial reconstruction techniques, Fourier wavefront reconstruction techniques, Fourier analysis of the spot frequency in frequency space, or the like. Correction of the retinal image may similarly be effected by a variety of standard optical error correction devices (including selecting among alternatively lenses of different powers and astigmatic orientations by rotation of a turret, movement of optical structures along and/or across the optical path so as to vary their power, using optical assemblies similar to those included in commercially available phoropters, and the like) or new optical power variation techniques (such as varying fluid focus lenses, or the like).

In another aspect, the invention provides a wavefront measurement method for measurement of an eye. The eye has optical tissues with a sphero-cylindrical error and irregular aberration. The method comprises directing an image onto a retina, and propagating the retinal image from the retina through the optical tissues. At least a portion of the retinal image is directed from the optical tissues to a first lenslet array having a first pitch so as to generate a first array pattern of retinal images. A sphero-cylindrical error of the eye is determined in response to the first pattern. The determined sphero-cylindrical error is corrected in the retinal image, and at least a portion of the corrected retinal image is directed to a second lenslet array having a second pitch so as to generate a second pattern of retinal images. The second pitch is finer than the first pitch. The irregular aberration of the eye is determined using the second pattern.

In yet another aspect, the invention provides a system for measurement of an eye, the eye having a retina and optical tissues with a sphero-cylindrical error and irregular aberration. The system comprises an illumination source oriented at an eye measurement location so as to form an image on the retina when the eye is at the eye measurement location. An optical train is oriented to propagate the retinal image from the optical tissues along one or more optical paths. The optical train includes correction optics. A first lenslet array is disposed along the optical path(s), the first lenslet array having a first pitch so as to generate a first array pattern of retinal images. A second lenslet array is disposed along the optical path(s), the second lenslet array having a second pitch so as to generate a second array pattern of retinal images. The second pitch is finer than the first pitch. A processor is coupled to the first and second patterns. The processor includes a feedback module coupling the first pattern to the correction optics so as to correct for the sphero-cylindrical error of the eye in the retinal image directed to the second lenslet array.

BRIEF DESCRIPTION OF THE DRAWINGS

FIG. 5 schematically illustrates an embodiment of a wavefront sensor system having a coarse pitch Shack-Hartmann wavefront sensor for determining and correcting standard refractive errors of the eye, and a fine pitch Shack-Hartmann sensor for wavefront reconstruction, determining the high-order apparitions, and the like.

FIG. 6 illustrates an alternative wavefront sensor system with fine and coarse pitch Shack-Hartmann sensors similar to those of FIG. 5, along with an adaptive optic in the form of a deformable mirror or the like.

DETAILED DESCRIPTION OF SPECIFIC EMBODIMENTS

The present invention may be particularly useful for enhancing the accuracy and efficacy of laser eye surgical procedures, such as photorefractive keratectomy (PRK), photherapeutic keratectomy (PTK), laser in situ keratomileusis (LASIK), and the like. Enhanced optical accuracy of refractive procedures may be provided by improving the methodology for deriving a corneal ablation or other refractive treatment program. The techniques described herein can be readily adapted for use new or with existing laser systems, wavefront sensors, and other optical measurement devices. While these systems, software, and methods are described primarily in the context of a laser eye surgery system, alternative eye treatment procedures and systems such as spectacle lenses, intraocular lenses, contact lenses, corneal ring implants, collagenous corneal tissue thermal remodeling, and the like may also be employed.

Wavefront sensors will typically measure aberrations and other optical characteristics of an entire optical system. The data from such a wavefront sensor may be used to generate a theoretical optical surface from an array of optical gradients. The theoretical optical surface need not precisely match an actual tissue surface, as the gradients will show the effects of aberrations which are actually located throughout the ocular tissue system.

In general, techniques for mathematical modeling an optical surface employ gradient fields comprising several localized gradients of an optical wavefront measured over an area of the optical surface. A localized gradient is often calculated by determining a location of a beam of light corresponding to a small portion of the optical surface. Several localized gradient measurements are made over the measurement area, and the location of each of several beams of light are be determined to map out a gradient field. Shack-Hartmann wavefront systems form several beams of light simultaneously. Wavefront measurement systems can optionally make use of adaptive optics systems such as a deformable mirror or the like. Adaptive optics systems are well-suited for measuring a patient's ocular aberrations, often by driving the deformable mirror to a configuration which compensates for the overall aberration of the eye.

Figure 1:
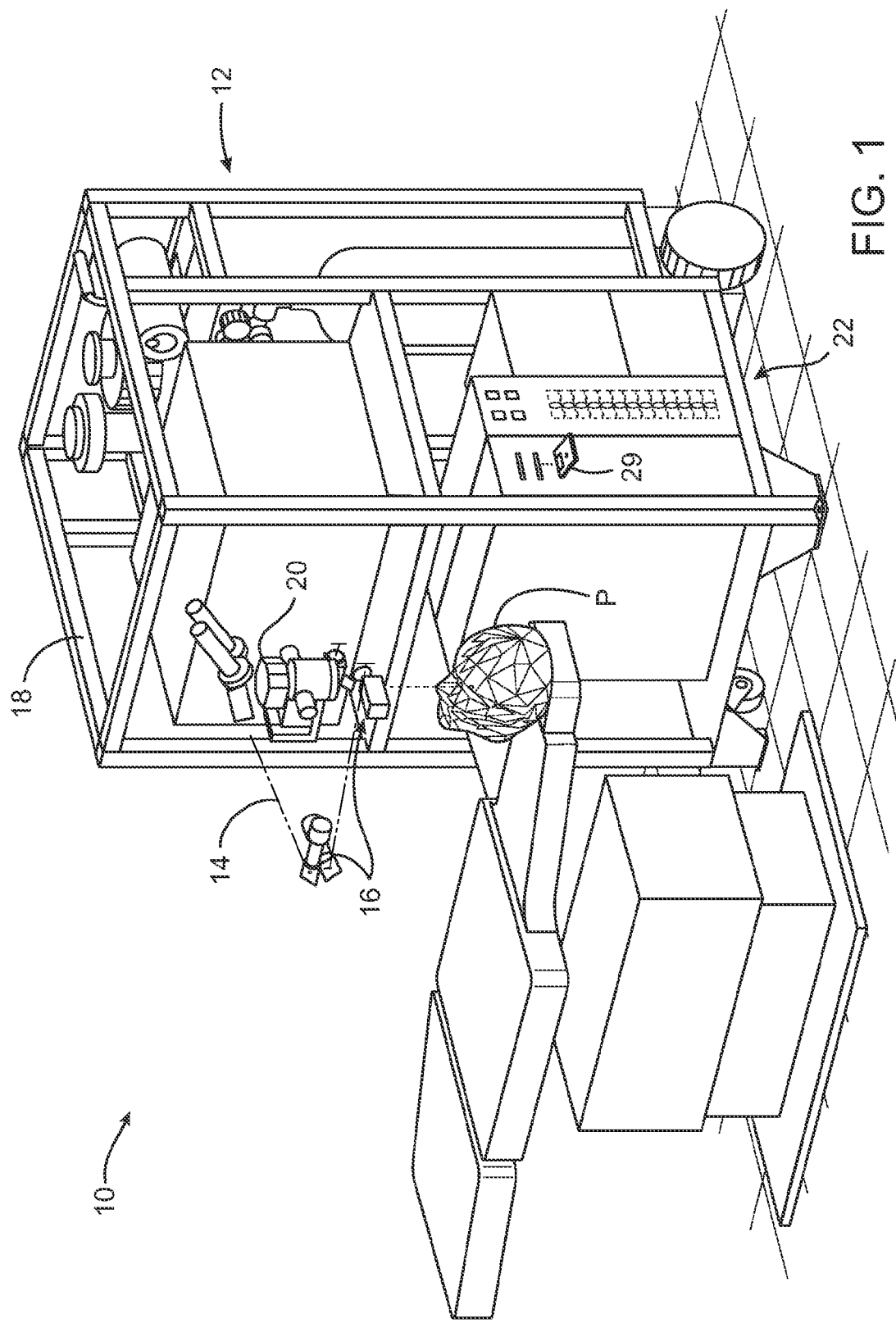
FIG. 1 illustrates a laser ablation system which can accept input from a wavefront measurement system embodying aspects of the present invention.

Referring now to FIG. 1, a laser eye surgery system 10 includes a laser 12 that produces a laser beam 14. Laser 12 is optically coupled to laser delivery optics 16, which directs laser beam 14 to an eye of patient P. A delivery optics support structure (not shown here for clarity) extends from a frame 18 supporting laser 12. A microscope 20 is mounted on the delivery optics support structure, the microscope often being used to image a cornea of the eye.

Laser 12 generally comprises an excimer laser, ideally comprising an argon-fluorine laser producing pulses of laser light having a wavelength of approximately 193 nm. Laser 12 will preferably be designed to provide a feedback stabilized fluence at the patient's eye, delivered via laser delivery optics 16. Alternative sources of ultraviolet or infrared radiation may also be used, particularly those adapted to controllably ablate the corneal tissue without causing significant damage to adjacent and/or underlying tissues of the eye. In some embodiments, the laser beam source employs a solid state laser source having a wavelength between 193 and 215 nm. Although an excimer laser is the illustrative source of an ablating beam, other lasers may be used.

Laser 12 and laser delivery optics 16 will generally direct laser beam 14 to the eye of patient P under the direction of a computer system 22. Computer system 22 will often selectively adjust laser beam 14 to expose portions of the cornea to the pulses of laser energy so as to effect a predetermined sculpting of the cornea and alter the refractive characteristics of the eye. In many embodiments, both laser 12 and the laser delivery optical system 16 will be under control of computer system 22 to effect the desired laser sculpting process, with the computer system effecting (and optionally modifying) the pattern of laser pulses. The pattern of pulses may be summarized in machine readable data of tangible media 29 in the form of a treatment table, and the treatment table may be adjusted according to feedback input into computer system 22 from an automated image analysis system (or manually input into the processor by a system operator) in response to real-time feedback data provided from an ablation monitoring system feedback system. The laser treatment system 10, and computer system 22 may continue and/or terminate a sculpting treatment in response to the feedback, and may optionally also modify the planned sculpting based at least in part on the feedback.

Additional components and subsystems may be included with laser system 10, as should be understood by those of skill in the art. For example, spatial and/or temporal integrators may be included to control the distribution of energy within the laser beam. Other ancillary components of the laser surgery system are known in the art. Suitable systems include commercially available refractive laser systems such as those manufactured and/or sold by Alcon, Bausch & Lomb, Nidek, WaveLight, LaserSight, Schwind, Zeiss Meditec, and the like.

Figure 2:
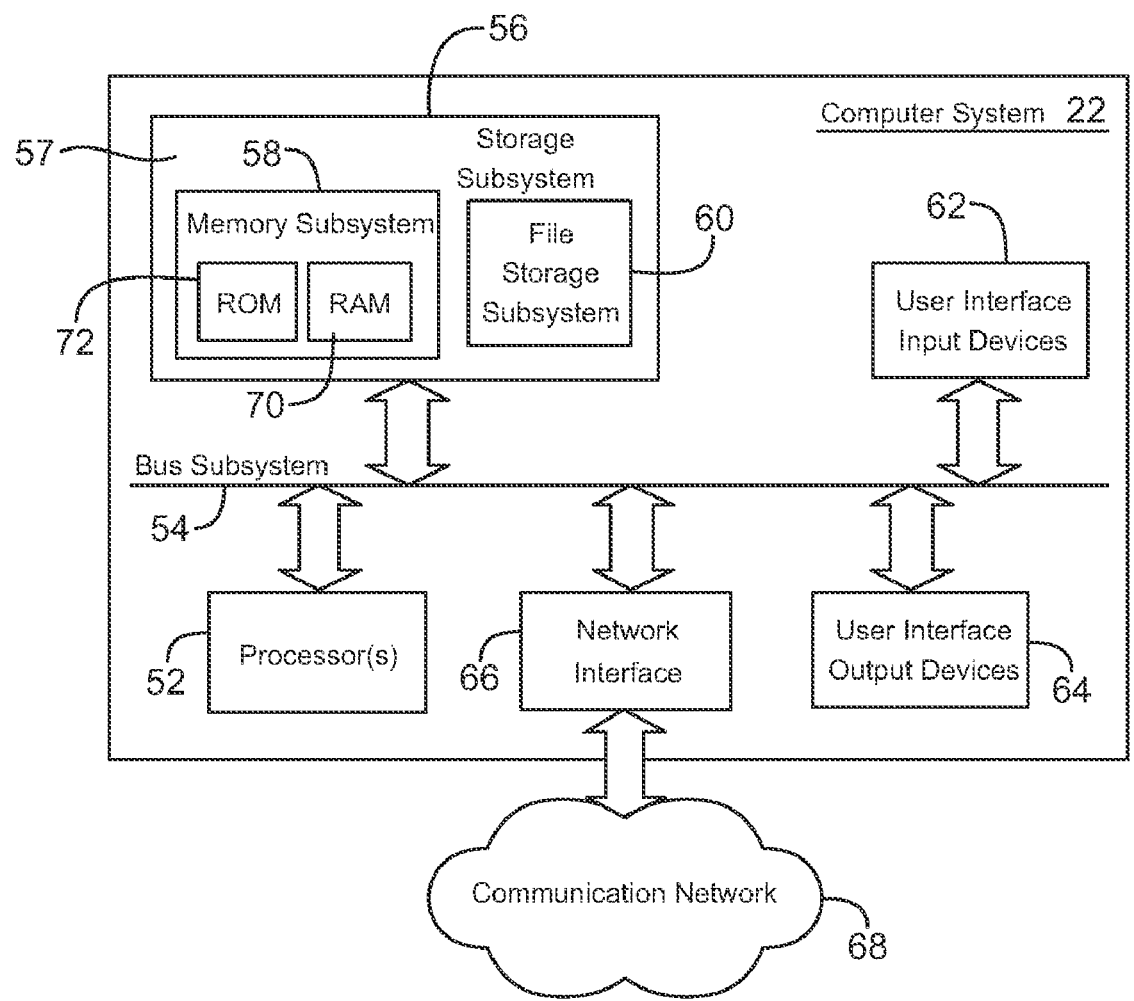
FIG. 2 illustrates a simplified computer system which can be used with the laser ablation system and/or a wavefront system.

FIG. 2 is a simplified block diagram of an exemplary computer system 22 that may be used by laser surgical system 10. Computer system 22 typically includes at least one processor 52 which may communicate with a number of peripheral devices via a bus subsystem 54. These peripheral devices may include a storage subsystem 56, comprising a memory subsystem 58 and a file storage subsystem 60, user interface input devices 62, user interface output devices 64, and a network interface subsystem 66. Network interface subsystem 66 provides an interface to outside networks 68 and/or other devices, such as the wavefront measurement system 30.

User interface input devices 62 may include a keyboard, pointing devices such as a mouse, trackball, touch pad, or graphics tablet, a scanner, foot pedals, a joystick, a touch-screen incorporated into a display 28, audio input devices such as voice recognition systems, microphones, and other types of input devices. User input devices 62 will often be used to download a computer executable code from a tangible storage media 29 embodying any of the methods described herein.

User interface output devices 64 may include display 28, a printer, a fax machine, or non-visual displays such as audio output devices. The display may be a cathode ray tube (CRT), a flat-panel device such as a liquid crystal display (LCD), a projection device, or the like. The display may also provide a non-visual display such as via audio output devices.

Storage subsystem 56 stores the basic programming and data constructs that provide the functionality of the various embodiments of the methods described herein. For example, a database and modules implementing the functionality of the methods, as described herein, may be stored in storage subsystem 56. These software modules generally are generally executed by processor 52. In a distributed environment, the software modules may be stored on a plurality of computer systems and executed by processors of the plurality of computer systems. Storage subsystem 56 typically comprises memory subsystem 58 and file storage subsystem 60.

Memory subsystem 58 typically includes a number of memories including a main random access memory (RAM) 70 for storage of program instructions and data during program execution and a read only memory (ROM) 72 in which fixed instructions are stored. File storage subsystem 60 provides persistent (non-volatile) storage for program and data files, and may include tangible storage media 29 (FIG. 1) which may optionally embody wavefront sensor data, wavefront gradients, a wavefront elevation map, a treatment map, and/or an ablation table. File storage subsystem 60 may include a hard disk drive, a floppy disk drive along with associated removable media, a Compact Digital Read Only Memory (CD-ROM) drive, an optical drive, DVD, CD-R, CD-RW, solid-state removable memory, and/or other removable media cartridges or disks including flash RAM. One or more of the drives may be located at remote locations on other connected computers at other sites coupled to computer system 22. The modules implementing the functionality of the techniques described herein may be stored by file storage subsystem 60. Storage sub system 56 can include any computer readable storage medium 57. For example, computer readable storage medium 57 can include any computer readable storage medium described in the memory subsystem and any computer readable storage medium described in the file storage system. For example, computer readable storage medium 57 can include temporary storage in the random access memory.

Bus subsystem 54 provides a mechanism for letting the various components and subsystems of computer system 22 communicate with each other as intended. The various subsystems and components of computer system 22 need not be at the same physical location but may be distributed at various locations within a distributed network. Although bus subsystem 54 is shown schematically as a single bus, alternate embodiments of the bus subsystem may utilize multiple busses.

Computer system 22 itself can be of varying types including a personal computer, a portable computer, a workstation, a computer terminal, a network computer, a control system in a wavefront measurement system or laser surgical system, a mainframe, or any other data processing system. Due to the ever-changing nature of computers and networks, the description of computer system 22 depicted in FIG. 2 is intended only as a specific example illustrating one embodiment. Many other configurations of computer system 22 are possible having more or less components than the computer system depicted in FIG. 2.

Figure 3:
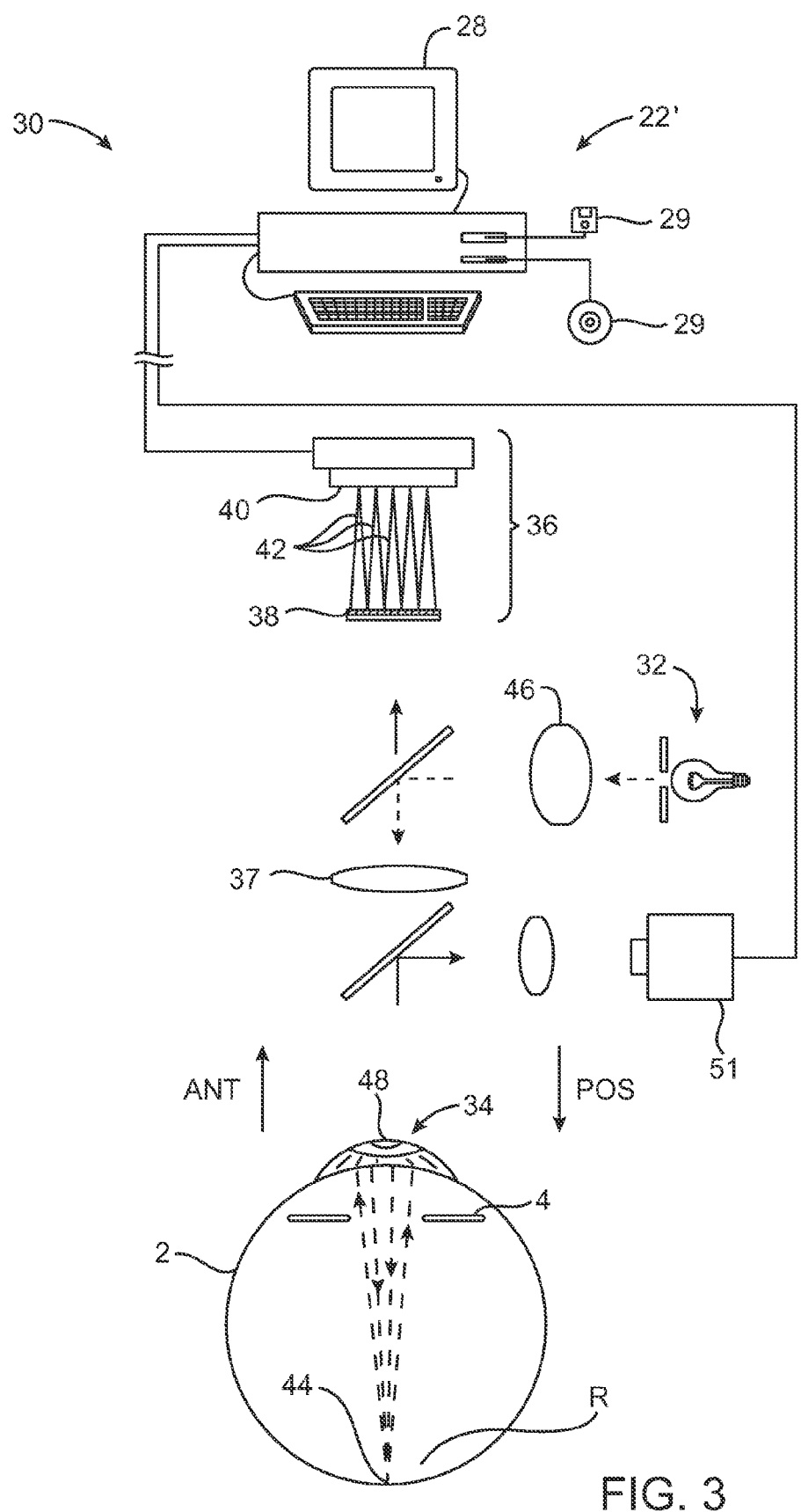
FIG. 3 illustrates a wavefront measurement system for modification according to the techniques described herein.

Referring now to FIG. 3, one embodiment of a wavefront measurement system 30 is schematically illustrated in simplified form. In very general terms, wavefront measurement system 30 is configured to sense local slopes of a gradient map exiting the patient's eye. Wavefront system 30 generally can include a lenslet array to sample the gradient map uniformly over an aperture, which is typically the exit pupil of the eye. Thereafter, the local slopes of the gradient map can be analyzed so as to reconstruct the wavefront surface or map.

More specifically, wavefront measurement system 30 can include an illumination source 32, such as a laser, which projects an image of the source through optical tissues 34 of eye E so as to form an image 44 upon a surface of retina R. Image 44 can comprise a very tiny spot of light and can be formed by imaging light passing through an aperture positioned near source 32. The image from retina R is transmitted by the optical system of the eye (e.g., optical tissues 34) and imaged onto a wavefront sensor 36 by system optics 37. The wavefront sensor 36 communicates signals to a computer system 22' for measurement of the optical errors in the optical tissues 34 and/or determination of an optical tissue ablation treatment program. Computer 22' may include tangible media embodying instructions or code for characterizing a surface, and/or for the other methods described herein. For example, instructions measuring a wavefront elevation profile by mapping data to signals in transform space and mapping the signals in transform space to the wavefront elevation profile. Computer 22' may include the same or similar hardware as the computer system 22 illustrated in FIGS. 1 and 2. Computer system 22' may be in communication with computer system 22 that directs the laser surgery system 10. If desired, data from wavefront sensor 36 may be transmitted to a laser computer system 22 via tangible media 29, via an I/O port, via an networking connection 66 such as an intranet or the Internet, a local area network (LAN) or the like.

Wavefront sensor 36 generally comprises a lenslet array 38 and an image sensor 40. As the image from retina R is transmitted through optical tissues 34 and imaged onto a surface of image sensor 40 and an image of the eye pupil P is similarly imaged onto a surface of lenslet array 38, the lenslet array separates the transmitted image into an array of beamlets 42, and (in combination with other optical components of the system) images the separated beamlets on the surface of sensor 40. Sensor 40 typically comprises a charged couple device or "CCD," and senses the characteristics of these individual beamlets, which can be used to determine the characteristics of an associated region of optical tissues 34. In particular, where image 44 comprises a point or small spot of light, a location of the transmitted spot as imaged by a beamlet can directly indicate a local gradient of the associated region of optical tissue. In alternate embodiments, the sensor can comprise a linear array detector, orthogonal linear array detectors, a position sensing detector or a quadrant detector.

Eye E generally defines an anterior orientation ANT and a posterior orientation POS. Illumination source 32 generally projects an image in a posterior orientation through optical tissues 34 onto retina R as indicated in FIG. 3. Optical tissues 34 again transmit light reflected from image 44 from the retina anteriorly toward wavefront sensor 36. As image 44 is actually formed on retina R, image 44 may be distorted by any imperfections in the eye's optical system. Optionally, illumination source projection optics 46 may be configured or adapted to decrease any distortion of image 44.

In some embodiments, illumination source optics 46 may decrease lower order optical errors by compensating for spherical and/or cylindrical errors of optical tissues 34. Illumination source optics 46 may include variable, adjustable, or selectable sphero-cylindrical refractive correction optics. Higher order optical errors of the optical tissues may also be compensated through the use of an adaptive optics system, such as a deformable mirror (described below). Use of an illumination source 32 selected to define a point or small spot at image 44 upon retina R may facilitate the analysis of the data provided by wavefront sensor 36. Distortion of image 44 may be limited by transmitting a source image through a central region 48 of optical tissues 34 which is smaller than a pupil 50, as the central portion of the pupil may be less prone to optical errors than the peripheral portion. Regardless of the particular illumination source structure, it will be generally be beneficial to have a well-defined and accurately formed image 44 on retina R.

The wavefront data may be stored in a computer readable medium 29 or a memory of the wavefront sensor system 30 in three separate arrays containing 1) the light spot pattern, 2) the x and y wavefront gradient values obtained from image spot analysis of the Shack-Hartmann sensor images, and 3) the x and y pupil center offsets from the nominal center of the Shack-Hartmann lenslet array, as measured by the pupil camera 51 (FIG. 3) image. Such information can contain the information on the wavefront error from one or more wavefront measurements of the eye and may be sufficient to reconstruct the wavefront or any portion of it. In other embodiments, the wavefront data may be stored in a memory of the wavefront sensor system in a single array or multiple arrays. In many embodiments additional patient data can be stored such as manifest patient refraction, subjective patient needs and preferences, and data measured with other instruments. While the computer readable medium or memory is shown with respect to the wavefront sensor system, additional memory and computers can be used. For example, computers sharing information over the local area network (LAN), and the intranet, and the Internet.

While methods will generally be described herein with reference to sensing of an image 44, a series of wavefront sensor data readings may be taken. For example, a time series of wavefront data readings may help to provide a more accurate overall determination of the ocular tissue aberrations. As the ocular tissues can vary in shape over a brief period of time, a plurality of temporally separated wavefront sensor measurements can avoid relying on a single snapshot of the optical characteristics as the basis for a refractive correcting procedure. Still further alternatives are also available, including taking wavefront sensor data of the eye with the eye in differing configurations, positions, and/or orientations. For example, a patient will often help maintain alignment of the eye with wavefront measurement system 30 by focusing on a fixation target. By varying a position of the fixation target as described in that reference, optical characteristics of the eye may be determined while the eye accommodates or adapts to image a field of view at a varying distance and/or angles. The coarse pitch lenslet array and/or associated coarse pitch array patterns described herein may be particularly well suited for measurement of accommodation when an optical distance to the fixation target is changed. More specifically, the smaller number of images or spots in the coarse pattern may significantly increase the speed and ease of accommodation measurements and calculations such as those more fully described in PCT patent application serial No. PCT/US05/21591, entitled "Correction of Presbyopia Using Adaptive Optics and Associated Methods" and filed on Jun. 17, 2005, the full disclosure of which is incorporated herein by reference.

The location of the optical axis of the eye may be verified by reference to the data provided from a pupil camera 52. In the exemplary embodiment, pupil camera 52 images pupil 50 so as to determine a position of the pupil for registration of the wavefront sensor data relative to the optical tissues.

Figure 4:
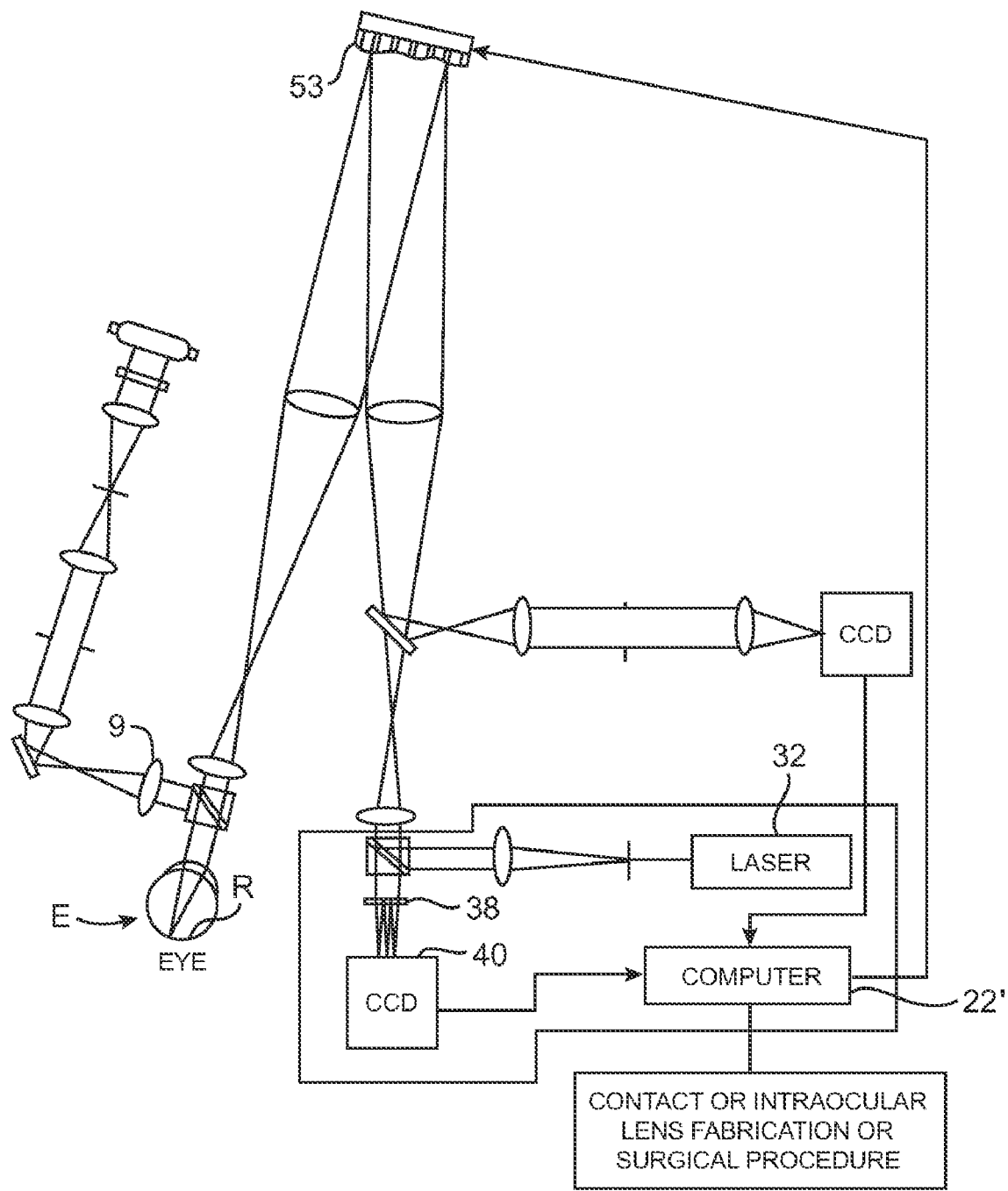
FIG. 4 illustrates an alternative wavefront measurement system for incorporating aspects of the present invention.

An alternative embodiment of a wavefront measurement system is illustrated in FIG. 4. The major components of the system of FIG. 4 are similar to those of FIG. 3. Additionally, FIG. 4 includes an adaptive optics system 53 in the form of a deformable mirror. The source image is reflected from deformable mirror 98 during transmission to retina R, and the deformable mirror is also along the optical path used to form the transmitted image between retina R and imaging sensor 40. Deformable mirror 98 can be controllably deformed by computer system 22 to limit distortion of the image formed on the retina or of subsequent images formed of the images formed on the retina, and may enhance the accuracy of the resultant wavefront data. The structure and use of the system of FIG. 4 are more fully described in U.S. Pat. No. 6,095,651, the full disclosure of which is incorporated herein by reference.

The components of an embodiment of a wavefront measurement system for measuring the eye and ablations comprise elements of a VISX WaveScan® system, available from VISX, Incorporated of Santa Clara, Calif. One embodiment includes a WaveScan® system with a deformable mirror as described above. An alternate embodiment of a wavefront measuring system is described in U.S. Pat. No. 6,271,915, the full disclosure of which is incorporated herein by reference.

Figure 5:
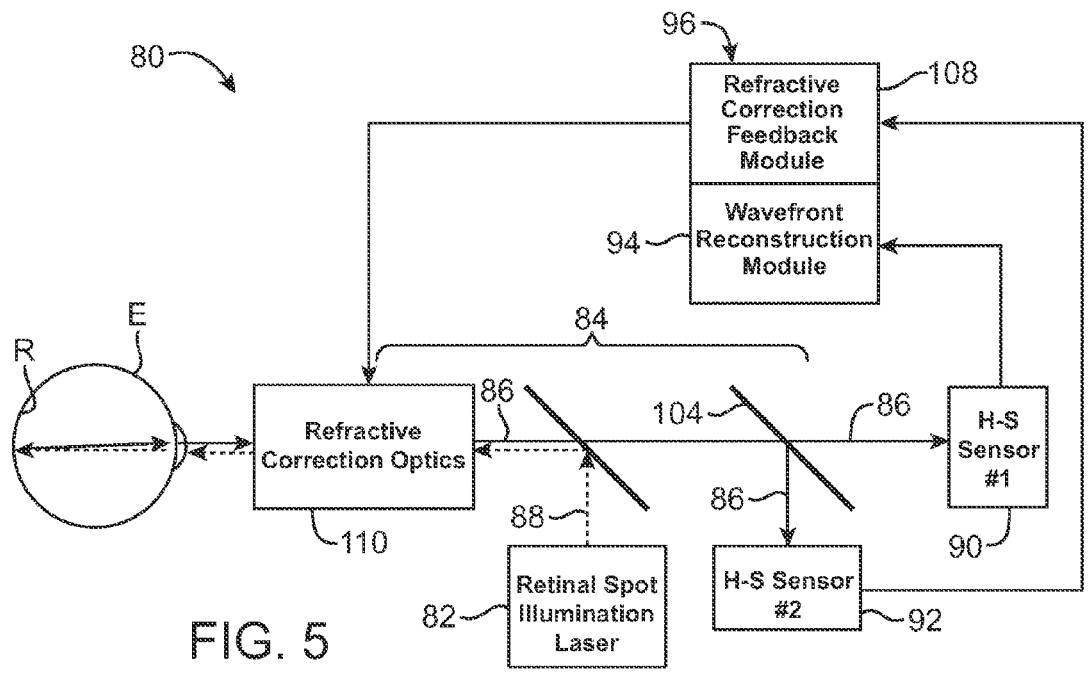

Referring now to FIG. 5, an integrated wavefront and autorefraction system 80 includes many individual components which are similar and/or derived from those described above regarding FIGS. 3 and 4. Retinal image illumination source 82 transmits a light (typically infrared) via an optical train 84 so as to form an image on retina R of eye E. The reflected light of retinal image R propagates forward through the optical tissues of eye E and is directed by optical train 84 along one or more optical path 86. While the illumination light 88 and path 86 may be shown as being slightly offset in FIGS. 5 and 6, it should be understood that the illumination light and retinal image path along at least a portion of optical train 84 may be coaxial.

In the embodiment of wavefront/autorefraction system 80 illustrated in FIG. 5, optical train 84 directs the retinal image to both a first Shack-Hartmann sensor 90 and a second Shack-Hartmann sensor 92. The lenslet array of each sensor 90, 92 will form an lenslet array pattern (in typically a spot image pattern) on a surface of the associated sensor, with the locations of each image within the pattern indicating a gradient of the wavefront (and hence the aberrations of the optical tissues in eye E). Hence, the first sensor 90 may be coupled to a wavefront reconstruction module 94 of a system processor 96 so as to characterize and analyze the aberrations of eye E.

Figure 7:
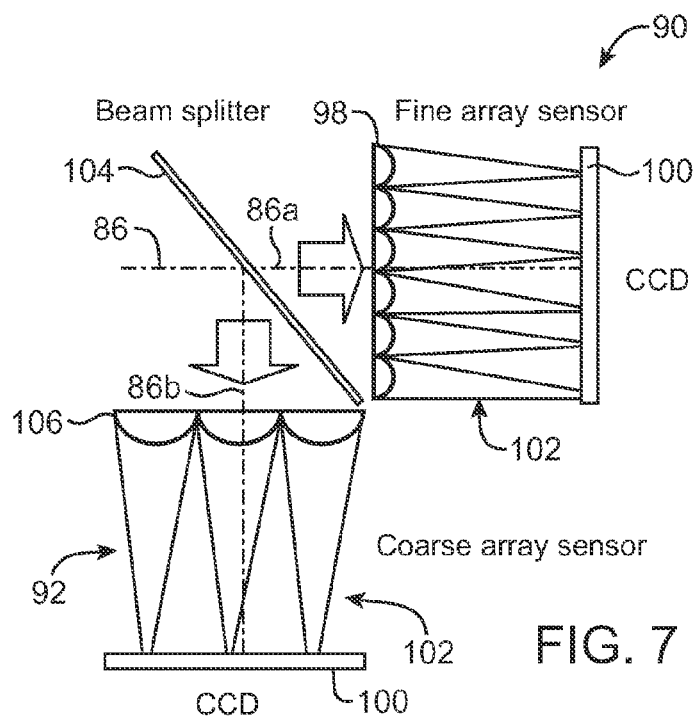
FIG. 7 is a schematic illustration of additional details of the fine and coarse pitch Shack-Hartmann sensors, showing the fine pitch lenslet array and coarse pitch lenslet array.

The components (including lenslet array 98 and image capture device 100) of first sensor 90 are shown in more detail (though still schematically) in FIG. 7, which also schematically illustrates the use of sensor 94 for generating and measuring a lenslet array pattern 102. Lenslet pattern array 102, typically comprising a spot pattern on the surface of image capture device 100, may be used (for example) for reconstruction of a wavefront using Zernicke polynomial reconstruction techniques, Fourier series reconstruction techniques, or other known wavefront analytical methodologies. Alternative reconstruction or analysis methods may also be employed, including those described in U.S. patent application Ser. No. 60/782,679, filed concurrently herewith, and entitled "Spatial Frequency Wavefront Sensor System and Method", the full disclosure of which is incorporated herein by reference.

The structure of processor 96 of integrated wavefront-autorefraction system 80 used for characterizing the wavefront or aberrations of eye E may include any of a wide variety of general purpose or specialized processing hardware, firmware, software, and the like. The various modules of processor 96 (including wavefront reconstruction module 94) will typically comprise hardware and/or software, with the software generally including machine readable programmable instruction for implementing the desired mathematical and other analytical method steps. The programming instructions may be embodied on any of a wide variety of tangible media (including volatile and non-volatile memory, magnetic recording media, optical recording media, or the like) and may optionally be communicated to processor 96 using a wide variety of data and programming communication modalities (including an Internet and Ethernet, a wireless transmitter, and the like). The modules of processor 96 may optionally be separated or integrated together in any of the wide variety of data processing architectures, programming architectures, and the like.

So as to provide relatively accurate details regarding irregular aberrations of eye E, the lenslet array 98 of first sensor 90 will typically have a relatively fine pitch, with a fairly large number of individual lenslets of the lenslet array being disposed within the optical path 86 of the retinal image. Lenslet array 98 may comprise a two-dimensional array of spherical lenslets, or may alternatively comprise a first series of cylindrical lenses aligned in parallel on one surface of the lenslet array, with another series of cylindrical lenslets aligned in parallel with each other and extending a cross the first series on the other surface of the lenslet array. Other alternative known Shack-Hartmann lenslet arrays or other new structures for forming lenslet array patterns may be employed.

The relatively fine pitch lenslet array of sensor 90 will typically have a pitch of about 400 μm or less. More generally, a fine pitch lenslet array will often have a significantly greater number of individual lenslets disposed within optical path 86 than a coarse pitch array, often having at least twice as many, and ideally having 5 times as many lenslets or more disposed within the optical path for accurate reconstruction of the wavefront. As used herein, the term "pitch" generally encompasses a measurement of the size of individual lenslets of an array, such a linear distance between centers of adjacent lenslets within the array. A "coarse" pitch lenslet array will generally have larger individual lenslets than a "fine" pitch lenslet array, so that if images are projected, with similar cross-sections, through a fine pitch lenslet array and a coarse pitch lenslet array, a greater number of the lenslets of the fine pitch array will be in the optical path. Similarly, a fine pitch image pattern will typically comprise significantly more individual images than a coarse pitch image pattern, with each of the individual images often comprising spot images similar to those of standard wavefront image patterns. Regardless of the specific number of individual lenslets in the course pitch array and/or images in the coarse pitch pattern, the fine pitch image pattern will typically have at least 20% more individual images than the coarse pitch image pattern.

In addition to first sensor 90, integrated wavefront-autorefraction system 80 has a second Shack-Hartmann sensor 92 with a coarser pitch lenslet array so as to provide information regarding the standard refractive error of eye E to processor 96. For example, as illustrated in FIG. 7, a beam splitter 104 optionally separates optical path 86 into a first optical path 86a associated with the first sensor, and a second optical path 86b associated with the second sensor 92. The portion of light from the retinal image which is directed along optical path 86b generates a relatively coarse lenslet array pattern 102 using a coarse pitch lenslet array 106. Coarse pitch 106 will typically have no more than half the number of lenslets within optical path 86b (as compared to the lenslets of fine pitch lenslet array 98 within optical path 86a), the coarse pitch array in many embodiments having one fifth the number of lenslets in the optical path or less. Exemplary coarse pitch lenslet arrays may have, for example, a pitch of about 1 mm or more.

Once again referring to FIG. 5, the data from the spot pattern of second sensor 92 will generally be transmitted to processor 96 for use by a refractive correction feedback module 108. Refractive correction feedback module 108 uses this incoming data to calculate an appropriate standard refractive correction, and implements that corrections along optical train 84 by sending signals to refractive correction optics 110. The refractive correction optics will typically include a variable or adjustable sphero-cylindrical optical assembly, which may comprise a plurality of alternatively selectable optics having differing sphero and/or cylindrical optical powers, an assembly of lenses which one or more of the lenses moves to alter the spherical and/or cylindrical optical powers of optical train 84, or the like. A wide variety of alternative optical refractive correction optics may be used, including well known standard devices or new assemblies for varying sphero-cylindrical optical power such as an exemplary variable fluid lens systems described in U.S. patent application Ser. No. 10/993,409, filed on Nov. 18, 2004, and entitled "Sphero-cylindrical Eye Refraction System Using Fluid to Focus Electrostatically Variable Lenses", the full disclosure of which is incorporated herein by reference.

To perform high precision measurements of the wavefront of the eye E, it is generally beneficial to correct or compensate for standard or sphero-cylindrical errors of the eye. While such correction may not compensate exactly for the entire amount of a standard refractive error of eye E, it is often beneficial for any residual or uncorrected refractive error to be less than about two diopters, often being less than about one diopter. As the information for driving refractive correction optics 110 is provided is by the second sensor 92, manual entry of the standard refractive error may be avoided, and perhaps more importantly, integrated wavefront/autorefraction system 80 need not delay the wavefront analysis while searching the Shack-Hartmann spot pattern during adjustments of the refractive correction optics so as to obtain the best focus of the spot images within the pattern.

The analysis performed by refractive correction feedback module 108 may optionally be similar to that performed by wavefront reconstruction module 94, with the feedback module optionally performing a wavefront reconstruction using Zernike techniques, Fourier analysis, or new approaches (such as the spatial frequency approach mentioned above). Alternatively, refractive feedback module 108 may employ a different analytical approach than that of the wavefront module. Regardless, the refractive correction feedback module will often analyze much fewer individual spot locations, gradients, and the like.

Once the signals to drive the refractive correction optics have been transmitted and implemented so that the first calculated standard refractive error the eye has been initially corrected, follow on measurement by second sensor 92 may be used to further refine the optical error measurement and more precisely adjust refractive corrective optics 110. More specifically, as the refractive corrective optics more and more accurately compensate for the standard error of the eye, the spot (or other image) on the retina R will be more and more accurately formed, the lenslet array pattern of second sensor 92 may be more precisely defined, and the overall autorefraction provided them by integrated system 80 may improve.

Referring still to FIGS. 5 and 7, beam splitter 104 generally divides the light of the retinal image by a desired ratio. In the Shack-Hartmann sensor, the intensity of the individual spots can generally be a function of both the total amount of light entering optical train 84, and also of the area of each lenslet of the associated lenslet array. The Shack-Hartmann lenslet array with a fine pitch will generally have a smaller lenslet areas than an array with a coarser pitch, so that the spot intensity may, if the same amount of light is directed to both sensors 90, 92, be less for the fine array of first sensory 90 than for the coarse of second sensor 92.

So as to take full advantage of the dual sensors 90, 92 of system 80, it will often be advantageous for beam splitter 104 to separate the total light of the retinal image so that more light enters the fine array of sensor 1 than to the coarse array of sensor 2. To make the spot intensities equal for the two sensors, the ratio of the light separation by beam splitter 104 should be such that the amount of light sent to the fine array is greater than the amount of light sent to the coarse array, ideally by at least the inverse ratio of their lenslet pitches squared. In other words, the light ratio between the fine pitch array and the coarse pitch array will preferably be at least the inverse of the area ratio of the lenslets of the fine pitch array to the lenslet area of the coarse pitch array. In practice, it may be better to send slightly more light to the fine pitch array than indicated by this calculation, as the fine pitch array will provide information which is used for analysis of the wavefront, calculation of an appropriate prescription for eye E, and the like. The coarse pitch array information, in contrast, may only be used to set the refractive correction optics 110 within system 80. The ability to preserve adequate signal strength for the fine pitch array sensor 90 may represent a significant advantage of system 80 when the two sensors will be used simultaneously. In many embodiments, fine pitch array 98 and coarse pitch array 106 may have nominally the same focal length, although they may also differ in other embodiments.

Figure 6:
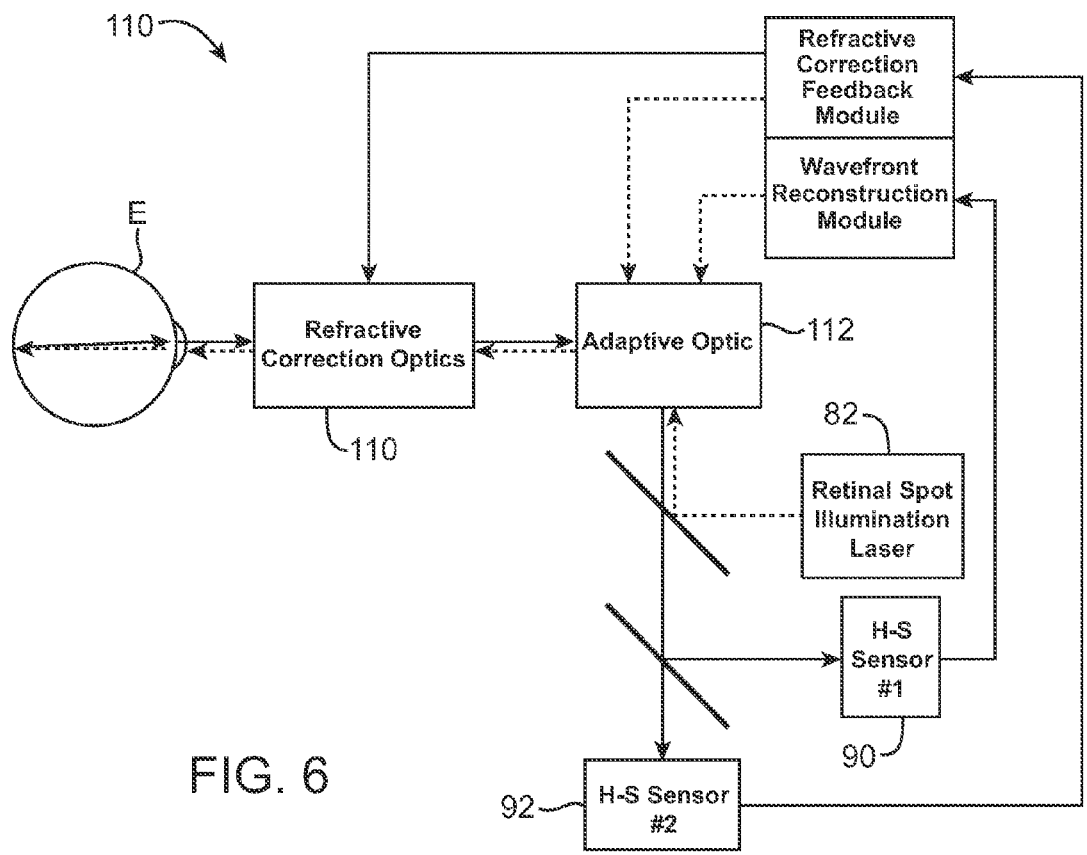

Referring now to FIG. 6, a wide variety of alternative integrated wavefront-autorefraction systems may be employed, including alternative system 110. In this embodiment, along with data from a coarse pitch Shack-Hartmann sensor 92 being used to adjust refractive correction optics 110 so as to compensate for standard refractive errors of eye E, data from the coarse pitch sensor or a fine pitch sensor 90 may be used to adjust an adaptive optic 112 (such as a deformable mirror or the like) so as to compensate for higher order aberrations of the eye. While the schematic illustrations of FIGS. 5 and 6 help explain the general arrangement and interaction between the system components, the locations of the beam splitters, one-way mirrors, and the like may be reconfigured in a wide variety of alternative configurations.

Figure 8A:
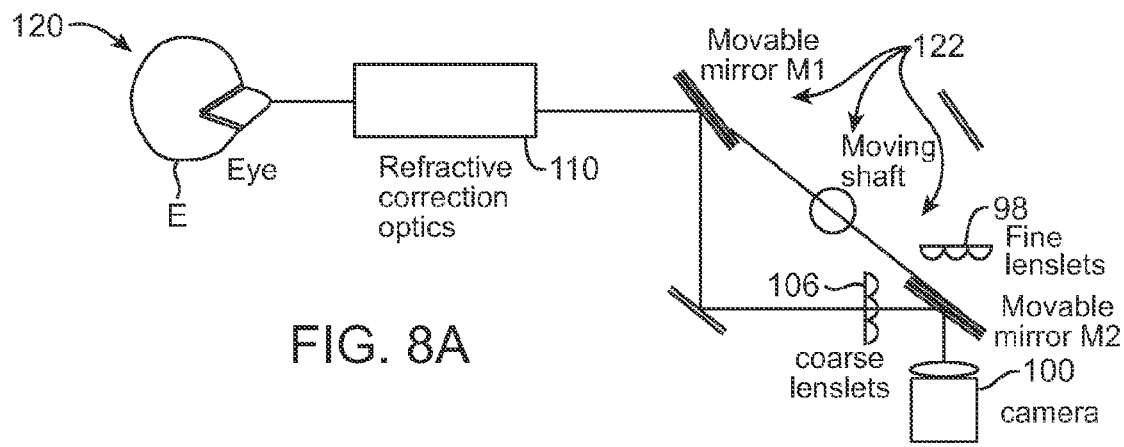
FIGS. 8A and 8B schematically illustrate an alternative wavefront system having fine and coarse pitch lenslet arrays, along with a pair of movable beam steering mirrors to couple the retinal image of the eye to a single image capture device through the coarse lenslet array (in the configuration of FIG. 8A) or through the fine lenslet array (in the configuration of FIG. 8B).
Figure 8B:
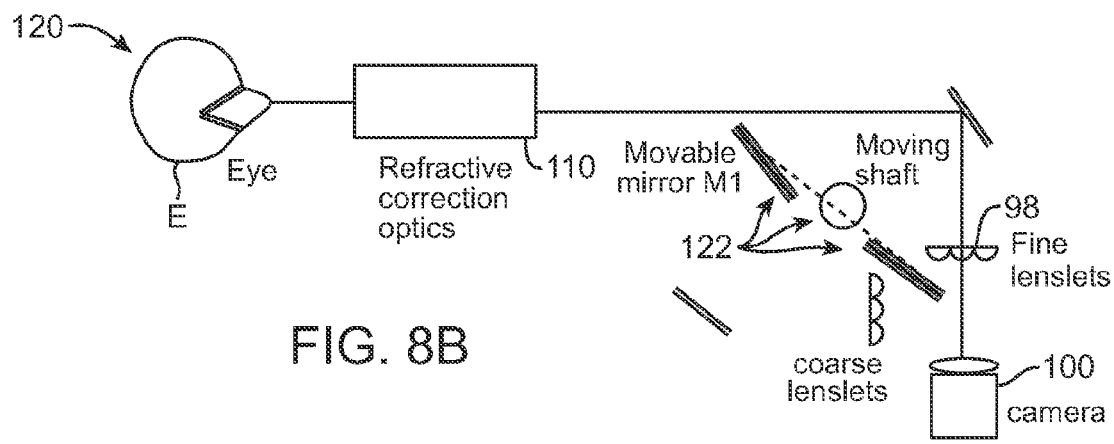

Referring now to FIGS. 8A and 8B, many of the components of a single camera wavefront/autorefraction system 120 are illustrated. The structures for forming an image of a light source on the retina of eye E are not shown for simplicity. Nonetheless, the light (typically infrared) reflected from the retina again propagates through the optical tissues of the eye and then through corrective optics 110. The corrected retinal image is transmitted by beam steering components of the optical train, which has two configurations. In the first configuration (as illustrated in FIG. 8A) a moveable mirror system 122 having first and second mirrors directs the retinal image light through a coarse lenslet array 106 and then to an image capture device 100. After sufficient data has been captured for determination of the standard refractive error of the eye an adjustment of refractive correction optics 110, the moveable mirror system 122 is reconfigured so that the light of the retinal image is transmitted through a fine lenslet array 98 and then to image captured device 100 (as illustrated in FIG. 8B). The fine lenslet array pattern formed on the sensor surface of image capture device 100 can then be used for wavefront measurement, using standard analysis of recorded Shack-Hartmann spots or the like.

When using single camera system 120, the light will generally be directed by the reconfigurable beam steering optics of moveable mirror system 122 through the coarse lenslet array 106. Images taken from the image capture device 100 will then be used to calculate and adjust the refractive correction optics 110. The adjustment to refractive correction optics 110 will often be performed largely in a single step, with follow-on adjustments as appropriate per the feedback and data obtained using the coarse lenslet array. Once light is directed to the fine pitch lenslet array 98, no further searching for the best focus spot pattern may be required. After the light passes through the fully adjusted correction optics 110, the light from the retinal image may still have some remaining refractive error, with that error preferably being within the dynamic range of the fine pitch lenslet array optical system. A new spot image pattern is captured by camera 100 while the moveable mirror system 122 directs light through the fine lenslet array 98, and high resolution wavefront analysis is performed using that fine spot pattern image.

Single camera system 120 may be particularly beneficial where the cost of a CCD camera (or other image capture device suitable for use in the system) is a major cost consideration, so that the ability to employ a single image capture device for both autorefraction and wavefront analysis helps limit the overall cost of the system. Once again, the lenslet arrays may, but need not have not only the same focal lengths in single camera system 120.

Figure 8C:
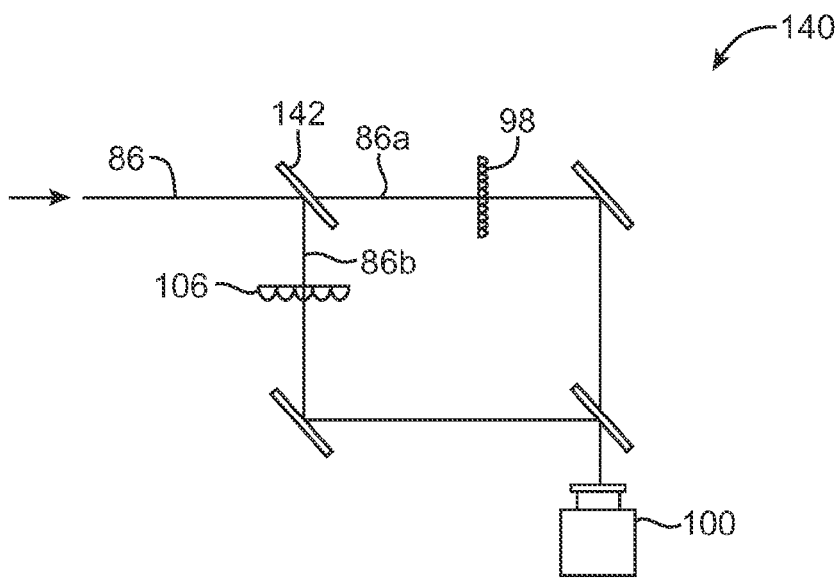
FIG. 8C schematically illustrates a further alternative wavefront system having fine and coarse pitch lenslet arrays, in which a majority of the light of the retinal image of the eye is directed through the fine lenslet array, and a minority of the light is directed through the coarse lenslet array, with the light from both lenslet arrays here being directed to a single image capture device.

Still further alternative embodiments may be provided, including a system 140 having a mirror 142 which directs a majority of the light from the retinal image through fine lenslet array 98, and a minority of the light from the retinal image through coarse pitch array 106, as illustrated in FIG. 8C. In these embodiment, mirror 142 may, for example, transmit about 80% of the light along optical path 86 to the fine lenslet array 98, and may reflect 20% of the light to coarse lenslet array 106. Although significantly less light reaches image capture device 100 from the coarse lenslet array, it may still be sufficient to allow determination of the regular optical error of the eye, optionally without use of a movable mirror.

Figure 9:
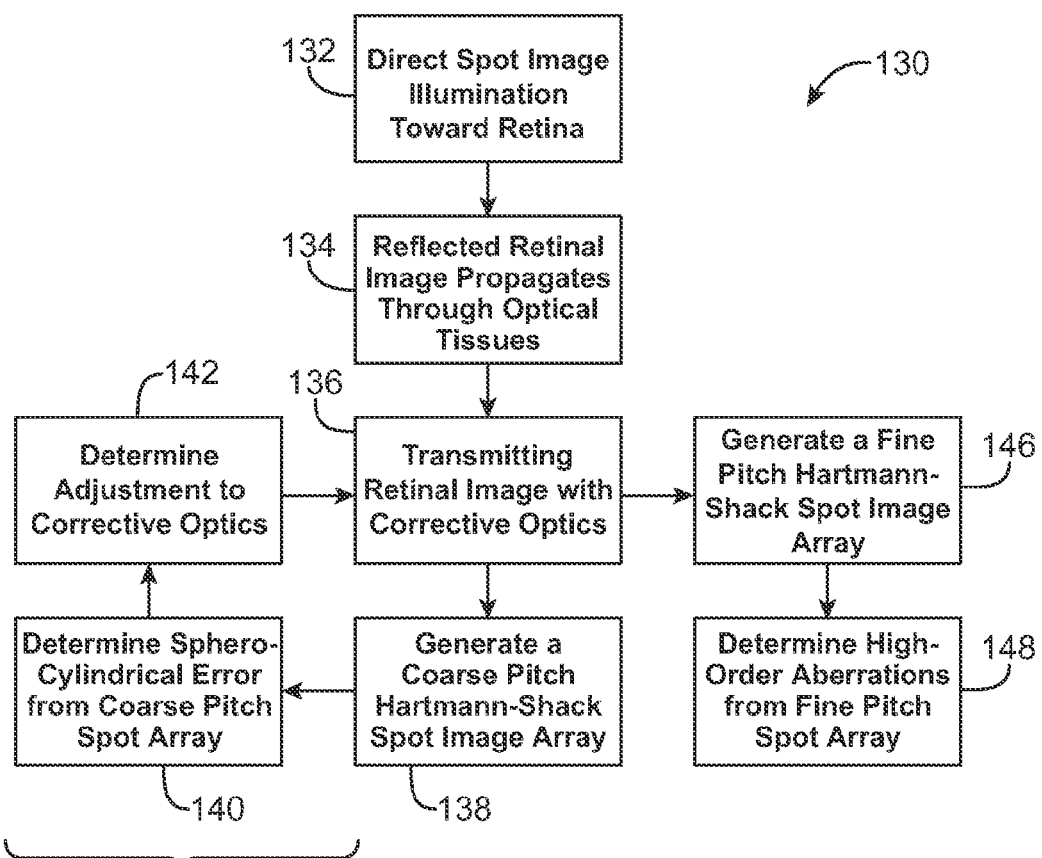
FIG. 9 schematically illustrates a flowchart and method for measurement of an eye in which standard refractive errors of the eye are determined using a coarse pitch spot array pattern and in which irregular aberrations are determined using a fine pitch spot array pattern.

Referring now to FIG. 9, an eye measurement method 130 may generally be used for characterizing or measuring an eye having optical tissues with both sphero-cylindrical errors and irregular aberrations. The method generally includes directing spot image illumination toward the retina 132. The reflected retinal image will generally propagate through the optical tissues 134, imposing both the sphero-cylindrical error and irregular aberration of the eye on the wavefront of the reflected retinal image. The retinal image propagates along an optical train, with corrective optics of the optical train transmitting the retinal image. A coarse pitch lenslet array pattern is generated 138 using the image from the corrective optics, and the sphero-cylindrical error of the optical tissues is determined 140 from the coarse pitch lenslet array pattern. The corrective optics are adjusted 142, and the coarse pitch pattern may again be analyzed to verify that the corrective optics are sufficiently compensating for the sphero-cylindrical error of the eye using a feedback loop 144.

Once the corrective optics have been adequately adjusted, a fine pitch lenslet array pattern is generated 146, and the high order aberrations of the eye are determined from that fine pitch pattern 148.

As each individual wavefront/autorefraction measurement may be completed without searching for the best focus in the fine pitch spot pattern, the overall time for the autorefraction/wavefront measurement may actually be less than for a standard wavefront measurement using known wavefront systems. It will often be advantageous to take a series of individual wavefront/autorefraction measurements of an eye, with the individual measurements being averaged or otherwise combined so as to determine an appropriate prescription for treating both the sphero-cylindrical and the high order aberrations of the eye using a laser refractive system, intraocular lenses, contact lens, or the like.

A variety of alternative methods and systems may be employed. For example, in some embodiments a single lenslet array may be used with variable zoom optics, moveable magnification optics, or the like so as to vary the number of lenslets of the lenslet array which are disposed within the optical path of the retinal image. This may effectively generate a coarse pitch lenslet array pattern by transmitting the retinal image through only a small number of the lenslets of the array.

While the exemplary embodiments have been described in some detail for clarity of understanding and by way of example, a variety of modifications, adaptations, and changes will be obvious to those of skill in the art and hence the scope of the present invention is limited solely by the appended claims.

What is claimed is:

1. A method for measurement of an eye, the eye having optical tissues with a sphero-cylindrical error and an irregular aberration, the method comprising:
   propagating a retinal image from the retina through the optical tissues;
   generating, from the image propagated through the tissues, a first array pattern having a plurality, N, of retinal images;
   determining the sphero-cylindrical error of the eye in response to the first pattern;
   compensating for the determined sphero-cylindrical error of the retinal image;
   generating, with the compensated retinal image, a second array pattern having a plurality, M, of retinal images, M being substantially greater than N; and
   determining the irregular aberration of the eye using the second pattern.

2. The method of claim 1, wherein the first pattern is generated using a first lenslet array having a first pitch, and wherein the second pattern is generated using a second lenslet array having a second pitch, the first pitch being coarser than the second pitch.

3. The method of claim 2, wherein the first pitch is sufficiently coarser than the second pitch that M is at least twice N.

4. The method of claim 2, wherein the first pitch is sufficiently coarser than the second pitch that M is at least 5 times N.

5. The method of claim 2, wherein the retinal image is directed from the tissues along at least one optical path, wherein N lenses of the first array are within the at least one optical path of the retinal image, and wherein M lenses of the second array are within the at least one optical path of the retinal image.

6. The method of claim 1, wherein the retinal image propagates from the eye while the eye is at an eye measurement location, and wherein the retinal image is directed to the first lenslet array and to the second lenslet array without moving the eye from the eye measurement location.

7. The method of claim 6, wherein a wavefront of the eye is measured without a search for a best focus spot pattern for the eye.

8. The method of claim 6, wherein retinal image is sequentially directed to the first lenslet array and then to the second lenslet array.

9. The method of claim 8, further comprising reconfiguring at least one beam steering optic so as to alternate between directing of the retinal image through the first lenslet array and through the second lenslet array.

10. The method of claim 9, wherein the beam is alternated by moving two mirrors so that the first and second patterns are sensed by a single image capture device.

11. The method of claim 1, wherein the first and second patters are generated simultaneously using first and second lenslet arrays, respectively.

12. The method of claim 11, wherein:
   the retinal image from the optical tissues comprises a first portion of light from the optical tissues directed to the first lenslet array, and a second portion of light from the optical tissue directed to the second lenslet array; and
   the second portion of light is substantially greater than the first portion of light.

13. The method of claim 12, wherein the second portion of light has at least four times the intensity of the first portion of light.

14. The method of claim 11, wherein each lenslet of the first lenslet array has a first area, wherein each lenslet of the second lenslet array has a second area, and further comprising transmitting the light from the optical tissues to a beam splitter, the beam splitter directing a first portion of light from the optical tissues to the first lenslet array and a second portion of the light from the optical tissues to the second lenslet array, a ratio of the second portion to the first portion being at least as large as a ratio of the first area to the second area.

15. The method of claim 1, further comprising:
   generating, from the compensated image, another first array pattern of retinal images;
   determining a revised sphero-cylindrical error of the eye in response to the other first pattern; and
   adjusting the compensation for the revised sphero-cylindrical error of the retinal image, so that the first pattern is used in a sphero-cylindrical feedback compensation loop.

16. A wavefront measurement method for measurement of an eye having optical tissues with a sphero-cylindrical error and irregular aberration, the method comprising:
   directing an image onto a retina;
   propagating the retinal image from the retina through the optical tissues;
   directing at least a portion of the retinal image from the optical tissues to a first lenslet array having a first pitch so as to generate a first array pattern of retinal images;
   determining the sphero-cylindrical error of the eye in response to the first pattern;
   correcting for the determined sphero-cylindrical error in the retinal image;
   directing at least a portion of the corrected retinal image to a second lenslet array having a second pitch so as to generate a second pattern of retinal images, the second pitch being finer than the first pitch; and determining the irregular aberration of the eye using the second pattern.

17. A system for measurement of an eye, the eye having a retina and optical tissues with a sphero-cylindrical error and irregular aberration, the system comprising:

an illumination source oriented at an eye measurement location so as to form an image on the retina when the eye is at the eye measurement location;

an optical train oriented to propagate the retinal image from the optical tissues and along at least one optical path, the optical train including compensation optics;

a first lenslet array disposed along one or more of the at least one optical path, the first lenslet array having a first pitch so as to generate a first array pattern of retinal images;

a second lenslet array disposed along one or more of the at least one optical path, the second lenslet array having a second pitch so as to generate a second array pattern of retinal images, the second pitch being finer than the first pitch;

a processor coupled to the first and second patterns, the processor including a feedback module coupling the first pattern to the correction optics so as to correct for the sphero-cylindrical error of the eye in the retinal image directed to the second lenslet array.

18. The system of claim 17, wherein the first pattern comprises N retinal images, wherein the first pattern comprises M retinal images, and wherein the first pitch is sufficiently coarser than the second pitch that M is at least twice N.

19. The system of claim 17, wherein the processor further includes a wavefront reconstruction module configured to determine the irregular aberrations of the eye from the second pattern.

20. The system of claim 19, wherein the processor is configured so that the wavefront of the eye is measured without a search for a best focus spot pattern for the eye.

21. The system of claim 17, wherein the optical train comprises at least one reconfigurable beam steering optic alternatably directing the retinal image through the first lenslet array or through the second lenslet array, wherein the processor is configured to adjust the correction optics so as to correct for the sphero-cylindrical error of the eye as determined using the first pattern, and to subsequently direct the retinal image from the adjusted correction optics to the second lenslet array.

22. The system of claim 20, wherein the beam steering optic(s) include two movable mirrors, the mirrors directing the first and second patterns to a single image capture device.

23. The system of claim 17, wherein the optical train comprises a beam splitter directing the retinal image toward the first lenslet array along a first optical path, and directing the retinal image toward the second lenslet array along a second optical path, so that the first and second patters can be generated simultaneously using first and second lenslet arrays.

24. The system of claim 23, wherein:

the retinal image directed along the first optical path comprises a first portion of light from the optical tissues, and the retinal image directed along the second optical path comprises a second portion of light from the optical tissue; and the beam splitter is configured so that the second portion of light is substantially greater than the first portion of light.

25. The system of claim 24, wherein the second portion of light has at least four times the intensity of the first portion of light.

26. The system of claim 24, wherein each lenslet of the first lenslet array has a first area, wherein each lenslet of the second lenslet array has a second area, and wherein the beamsplitter is configured so that a ratio of the second portion to the first portion is at least as large as a ratio of the first area to the second area.

27. The system of claim 17, wherein the processor comprises machine-readable programming instructions of the feedback module configured for:

generating, from the corrected image, another first array pattern of retinal images;

determining a revised sphero-cylindrical error of the eye in response to the other first pattern; and adjusting the correction for the revised sphero-cylindrical error of the retinal images.

* * * * *